(12) United States Patent
Hsish et al.

(10) Patent No.: US 8,597,209 B2
(45) Date of Patent: Dec. 3, 2013

(54) FOOT CORRECTING AND BALANCING SHOE ASSEMBLY AND METHOD FOR CORRECTING AND BALANCING USER'S FOOT

(75) Inventors: Chin-Hsing Hsish, Yongkang (TW); Tsung-Hsien Hsieh, Yongkang (TW); Ken-Tick Soh, Kuala Lumpur (MY); Tung-Chen Hsieh, Yongkang (TW)

(73) Assignee: Jun-Da Biotechnology Co., Ltd., Tainan (TW)

( * ) Notice: Subject to any disclaimer, the term of this patent is extended or adjusted under 35 U.S.C. 154(b) by 769 days.

(21) Appl. No.: 12/782,981

(22) Filed: May 19, 2010

(65) Prior Publication Data
US 2011/0288446 A1 Nov. 24, 2011

(51) Int. Cl.
*A61B 5/103* (2006.01)
*A43B 7/14* (2006.01)

(52) U.S. Cl.
USPC ................... 600/592; 36/155; 36/71; 36/159; 36/160; 36/161; 12/142 N

(58) Field of Classification Search
USPC ......... 36/155, 71, 159, 160, 161, 43, 44, 140, 36/142, 143, 144; 600/592; 12/142 N, 12/146 B, 146 M
See application file for complete search history.

(56) References Cited

U.S. PATENT DOCUMENTS

| | | | | |
|---|---|---|---|---|
| 1,417,989 | A * | 5/1922 | Gutmann | 36/159 |
| 2,732,636 | A * | 1/1956 | Amico | 36/160 |
| 3,339,555 | A * | 9/1967 | Rotko | 36/165 |
| 4,808,469 | A * | 2/1989 | Hiles | 428/318.6 |
| 4,813,157 | A * | 3/1989 | Boisvert et al. | 36/44 |
| 4,841,648 | A * | 6/1989 | Shaffer et al. | 36/43 |
| 6,510,626 | B1 * | 1/2003 | Greenawalt | 36/43 |
| 7,373,740 | B2 * | 5/2008 | Lo | 36/44 |

* cited by examiner

*Primary Examiner* — Ted Kavanaugh
(74) *Attorney, Agent, or Firm* — Pillsbury Winthrop Shaw Pittman, LLP

(57) ABSTRACT

A foot correcting and balancing shoe assembly includes at least one sole unit having an imaginary transverse line dividing the sole unit into front- and rear-half regions. The rear-half region includes left and right rear-half sections, and a heel area spanning rear portions of the left and right rear-half sections. A foot arch correction device is mounted detachably to the sole unit. At least one balancing pad is mounted detachably within the sole unit below the foot arch correction device, and at a predetermined location in at least one of the left and right rear-half sections to maintain foot balance for a user.

16 Claims, 13 Drawing Sheets

FOOT CORRECTING AND BALANCING SHOE ASSEMBLY AND METHOD FOR CORRECTING AND BALANCING USER'S FOOT

BACKGROUND OF THE INVENTION

1. Field of the Invention

This invention relates to a shoe assembly, more particularly to a foot correcting and balancing shoe assembly and a method for correcting and balancing a user's foot when the foot correcting and balancing shoe assembly is worn by the user.

2. Description of the Related Art

Our feet have good flexibility and can bear the weight of our body. However, some foot arches are not normal, so that the distribution of pressure on the bottom of the foot is not balanced, gait is also affected, and the body's center of gravity is moved to an incorrect position. Thus, foot arch correction devices are developed to correct the foot arch of a user. However, since the foot is made up of many bones and joints, as one grows older, the muscles, ligaments, and joints tend to loosen and/or change, and many problems arise because of the pressure brought about by the body weight, especially if a portion(s) of the foot has been previously hurt. Under such circumstances, the use of a foot arch correction device is not sufficient to restore complete balance. Further, even when the foot arch correction device is providing the proper and necessary correction, the foot condition resulting from old habits may seem normal to some. Thus, after using the foot arch correction device for a certain period of time, a new imbalance and a new feeling of discomfort may be experienced.

SUMMARY OF THE INVENTION

Therefore, the object of the present invention is to provide a foot correcting and balancing shoe assembly and a method for correcting and balancing a user's foot when the foot correcting and balancing shoe assembly is worn by the user.

According to one aspect of this invention, a shoe assembly foot correcting and balancing shoe assembly, comprises at least one sole unit, a foot arch correction device, and at least one balancing pad. The sole unit has an imaginary transverse line dividing the sole unit into front- and rear-half regions. The rear-half region includes left and right rear-half sections, and a heel area spanning rear portions of the left and right rear-half sections. The foot arch correction device is mounted detachably to the sole unit. The balancing pad is mounted detachably within the sole unit below the foot arch correction device and at a predetermined location in at least one of the left and right rear-half sections to maintain foot balance for a user.

According to another aspect of this invention, a method for correcting and balancing a user's foot comprises the steps of: obtaining an initial footprint of the user's foot; analyzing the shape and the darkness of ink in the initial footprint of the user's foot to obtain initial information as to a location where the user's foot has foot imbalance; selecting one or more proper balancing pad(s) from a set of balancing pads and attaching the same to a sole unit of a foot correcting and balancing shoe assembly at the location where the user's foot has the foot imbalance; and allowing the user to wear the foot correcting and balancing shoe assembly.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
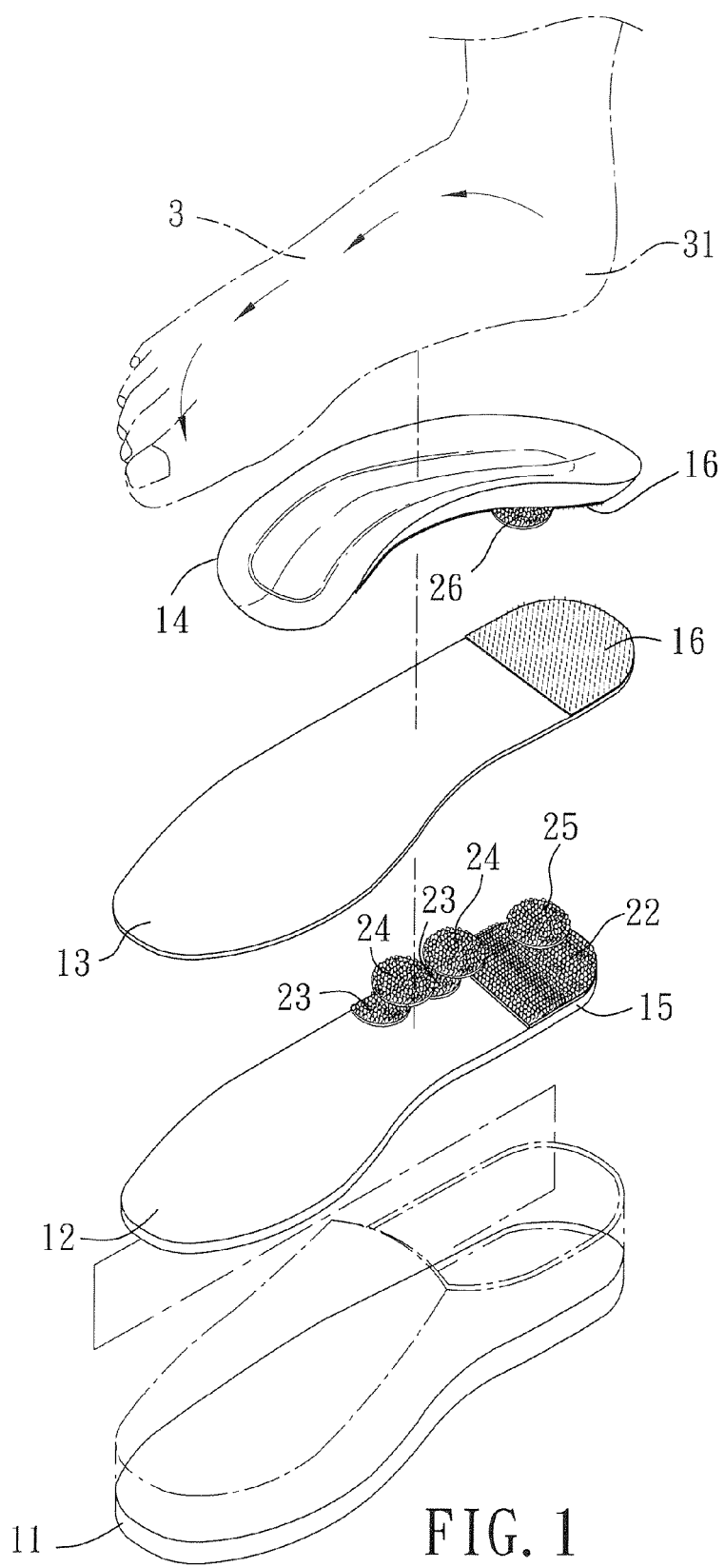
FIG. 1 is an exploded perspective view of a foot correcting and balancing shoe assembly according to the preferred embodiment of the present invention.

Before the present invention is described in greater detail, it should be noted that like elements are denoted by the same reference numerals throughout the disclosure.

Referring to FIGS. 1 to 24, a foot correcting and balancing shoe assembly according to the preferred embodiment of the present invention comprises a plurality of sole units, a foot arch correction device 14, and a set of balancing pads. Since the construction of the shoe assembly for the left and right feet of a user is symmetrical, only the foot correcting and balancing shoe assembly for the right foot 3 of the user is illustrated in the drawings.

The sole units include an outsole 11, an insole 12, and a sole liner 13. Each sole unit 11, 12, 13 has an imaginary transverse line (see FIG. 3) dividing a respective sole unit 11, 12, 13 into a front-half region 17 (see FIG. 3) and a rear half-region 18 (see FIG. 3). The rear half-region 18 includes left and right rear-half sections 182, 181 (see FIG. 3), and a heel area 15 spanning rear portions of the left and right rear-half sections 182, 181 and corresponding to the user's heel 31.

The foot arch correction device 14, in this embodiment, is configured as an arch-shaped support plate, and is mounted detachably to the sole liner 13, such that the sole liner 13 is disposed between the insole 12 and the foot arch correction device 14. Since the construction of the foot arch correction device 14 is not a main aspect of the present invention, a detailed description of the same is dispensed herewith for the sake of brevity. A rear edge of the foot arch correction device 14 is flush with a rear edge of the heel area 15. Two hook fasteners 16 are respectively adhered to a bottom face of the foot arch correction device 14 and a top face of the sole liner 13 to prevent relative movement therebetween, so that the foot arch correction device 14 not only can be immobilized, but also can be removed easily away from the sole liner 13.

The set of balancing pads includes a heel pad 22, at least one segment-shaped lateral supporting pad 23, at least one circular micro-adjustment pad 24, at least one circular rear adjustment pad 25, and at least one circular navicular bone supporting pad 26. Each of the lateral supporting pad 23, the micro-adjustment pad 24, the rear adjustment pad 25, and the navicular bone supporting pad 26 has a diameter ranging from 15 mm to 45 mm, and is provided with a loop fastener on a top surface thereof and an adhesive layer on a bottom surface thereof. The adhesive layer may be a piece of double-sided tape which can be easily adhered to another surface. Further, each of the lateral supporting pad 23, the micro-adjustment pad 24, and the rear adjustment pad may be mounted detachably to the left or right rear-half section 182, 181 of the insole 12 at a predetermined location so as to maintain foot balance for the user.

Taking for example a first foot type, where the user has a fallen foot arch, the set of the balancing pads required are one heel pad 22, two lateral supporting pads 23, two micro-adjustment pads 24, one rear adjustment pad 25, and one navicular bone supporting pad 26, as shown in FIG. 1. The balancing pads 22, 23, 24, 25 are attached to the insole 12, while the balancing pad 26 is attached to a bottom portion of the foot arch correction device 14. Alternatively, the balancing pads 22, 23, 24, 25, 26 may be attached to the outsole 11 or the sole liner 13, and the attachment is not limited to the aforesaid disclosure.

Figure 3:
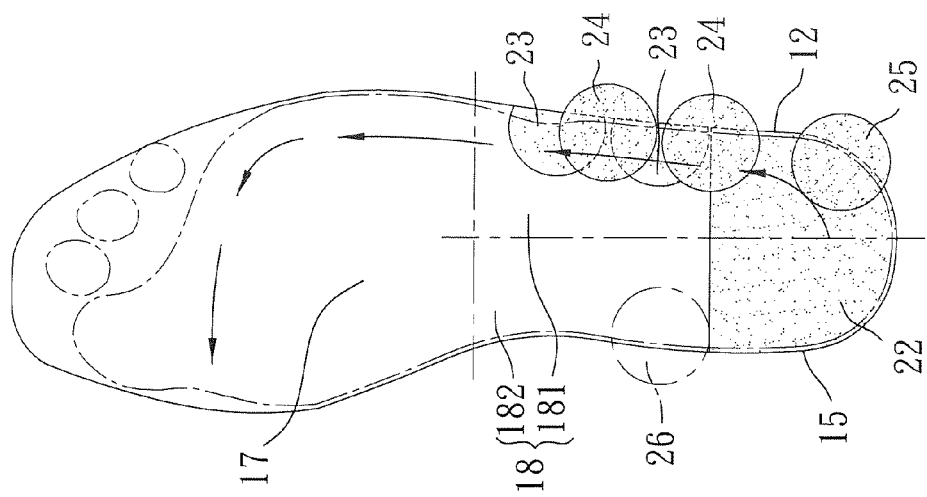
FIG. 3 shows balancing pad(s) attached to an insole according to the first preferred embodiment of a method of the present invention.
Figure 2:
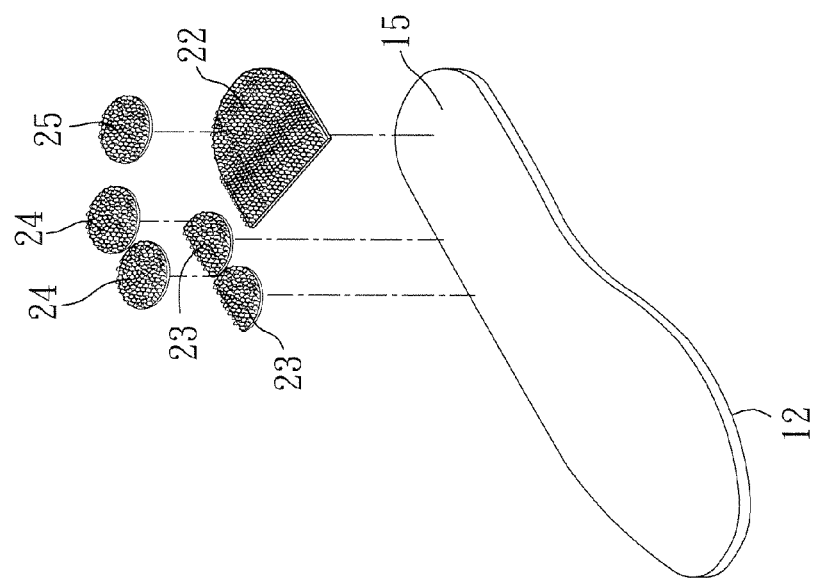
FIG. 2 is an exploded perspective view of a set of balancing pads of the preferred embodiment.

As shown in FIGS. 1 and 3, the heel pad 22 is attached to the heel area 15 of the insole 12, the lateral supporting pads 23 are attached side-by-side to the right rear-half section 181 of the insole 12 anteriorly of the heel pad 22, and have linear edges flush with an edge of an outer lateral side of the insole 12. One of the micro-adjustment pads 24 is attached to and spanning top surfaces of the two lateral supporting pads 23 and partially protrudes out of the outer lateral side of the insole 12. The other micro-adjustment pad 24 is attached to and spanning top surfaces of the heel pad 22 and the lateral supporting pad 23 that is adjacent to the heel pad 22, is side-by-side with said one of the micro-adjustment pads 24, and partially protrudes out of the outer lateral side of the insole 12. The rear adjustment pad 25 is attached to the top surface of the heel pad 22 at a rear outer portion thereof and partially protrudes out of the heel pad 22. The navicular bone supporting pad 26 is attached to the hook fastener 16, which is adhered to the bottom portion of the foot arch correction device 14, at a position corresponding to an inner lateral side of the insole 12 anteriorly of the heel pad 22.

A first preferred embodiment of the method for correcting and balancing a user's foot according to the present invention comprises steps I~VII and employs the foot correcting and balancing shoe assembly as described hereinbefore.

Step I

Figure 4:
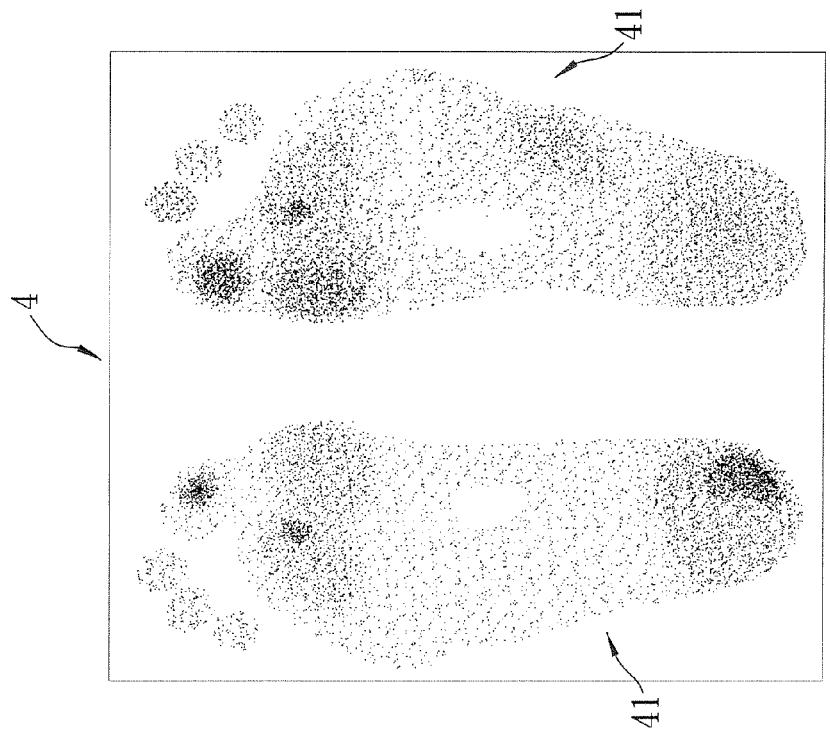
FIG. 4 is a schematic view of initial footprints of the user's feet obtained in the first preferred embodiment of the method of the present invention.

Initial footprints 41 of the user's left and right feet 3 (only the right foot is shown in FIG. 3) are obtained, and are printed on a sheet of paper 4, as shown in FIG. 4. A printing device (not shown) includes overlapping left and right boards, and a resilient fabric sheet disposed therebetween. The initial footprints 41 are obtained using the steps as outlined below.

1. The left and right boards are flipped open to reveal the resilient fabric sheet. The resilient fabric sheet is placed on the right board first if the left foot is to be printed, after which the ink is applied to the resilient fabric sheet by using a roller. The roller is moved back and forth so as to spread uniformly the ink on the resilient fabric sheet.

2. A blank sheet of paper 4 is folded lengthwise, and is placed on the left board with a left foot printing area facing upward.

3. The resilient fabric sheet is flipped toward the left board so as to impose upon the paper 4. The surface of the resilient fabric sheet having the ink faces a left foot printing area of the paper 4.

4. The user's left foot is then placed on a surface of the resilient fabric sheet that is opposite to that having the ink, while the user's right foot 3 is placed on the right board. The user must stand completely still at this time. If there is any movement, printing of the user's left foot must be repeated.

5. The user then squats so that the pressure borne by the left foot can be printed on the paper 4.

6. After the footprint 41 of the left foot is obtained, the left foot is first removed from the left board, after which the right foot 3 is removed from the right board. The resilient fabric sheet is then flipped to the right board away from the paper 4 to reveal an initial footprint 41 of the user's left foot. If the right foot 3 is removed first from the right board, the printing of the left foot must be repeated.

7. The left and right boards are then turned 180° relative to a horizontal surface so that the resilient fabric sheet is now located on the left board. The paper 4 is placed on the right board with a right foot printing area facing upward. Steps 3 to 6 are repeated. It should be noted that the height of squatting for the second time must be the same as that of the first time.

Step II

In this step, the shape and the darkness of ink in each of the initial footprints 41 of the user's feet 3 are analyzed to obtain initial information as to where the user's feet have foot imbalances.

Figure 5:
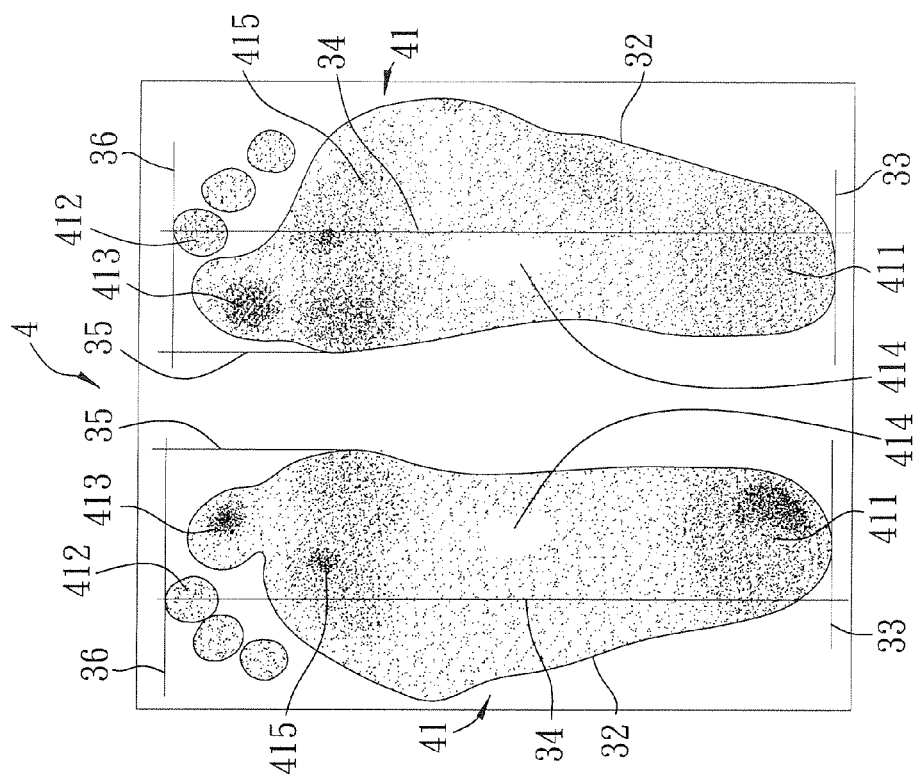
FIG. 5 is a view similar to FIG. 4, but illustrating a contour line drawn around a periphery of each initial footprint.

With reference to FIG. 5, the step of analyzing the shape and the darkness of the ink in each of the initial footprints 41 of the user's feet 3 includes the substeps as outlined below.

(i) A contour line 32 is drawn around a periphery of each initial footprint 41.

(ii) The following lines are drawn on each footprint 41: a first transverse reference line 33 that passes through a rear end of a heel thereof, a second transverse reference line 36 that passes through a front end of a toe thereof, a first longitudinal reference line 34 that passes centrally through the index toe 412 of each footprint 41, and a second longitudinal reference line 35 that passes through an inner lateral side of each footprint 41 that is proximate to the big toe 413 and that is parallel to the first longitudinal reference line 34. The first and second longitudinal reference lines 34, 35 are perpendicular to the first and second transverse reference lines 33, 36.

(iii) The contour lines 32 of the footprints 41 are analyzed to determine the foot arch type of each user's foot 3. If the width of the foot arch mid region 414 is large, the user's foot 3 has a fallen arch. If the foot arch mid region 414 is narrow or has a discontinuity, the user's foot 3 has a high arch. When it is observed that the foot arches of the left and right footprints 41 are incomplete, and the width of the foot arch mid regions 414 are excessively large, this means that the user's feet 3 have fallen arches.

(iv) Through an inspection of areas at the left (inner) and right (outer) sides of the first longitudinal reference line 34 of each footprint 41, and through an investigation as to whether the first longitudinal reference line 34 of each footprint 41 passes through the center of a heel region 411 or falls between the center and the inner lateral side of the footprint 41 or between the center and an outer lateral side of the footprint 41, a tilting direction of each footprint 41 is analyzed to determine whether the user's foot has a deviation or pronation problem. If the first longitudinal reference line 34 of each footprint 41 is located between the center and the outer lateral side of the footprint 41, this indicates that the body weight of the user deviates toward the inner lateral sides of the feet thereof.

(v) Since the foot pressure is distributed evenly in all regions of a normal foot, the darkness of the ink in each footprint 41 must be uniform if it is normal. If the darkness of the ink of the footprint 41 is uneven, the distribution of the foot pressure will be disuniform. The foot pressure is high where the color of the ink is dark. Hence, by observing the darkness of the ink in each footprint 41, it is possible to determine whether the pressure is concentrated at the front or rear or toward the inner or outer lateral side of the footprint 41. If the ink at the heel region 411 is dark, this means that the center of gravity is at the rear of the user's foot. Further, if the shading of the ink at the inner side of the first longitudinal reference line 34 is darker than that at the right side thereof, this indicates that the foot pressure deviates toward the inner side, especially when the toe region 415 that is situated below the big toe 413 has ink shading that gradually becomes darker from the right side to the left side of the first longitudinal reference line 39. If the shading of the ink at the big toe 413 of the right footprint 41 is relatively dark, then it can be determined that the foot pressure is concentrated at the big toe 413.

Figure 6:
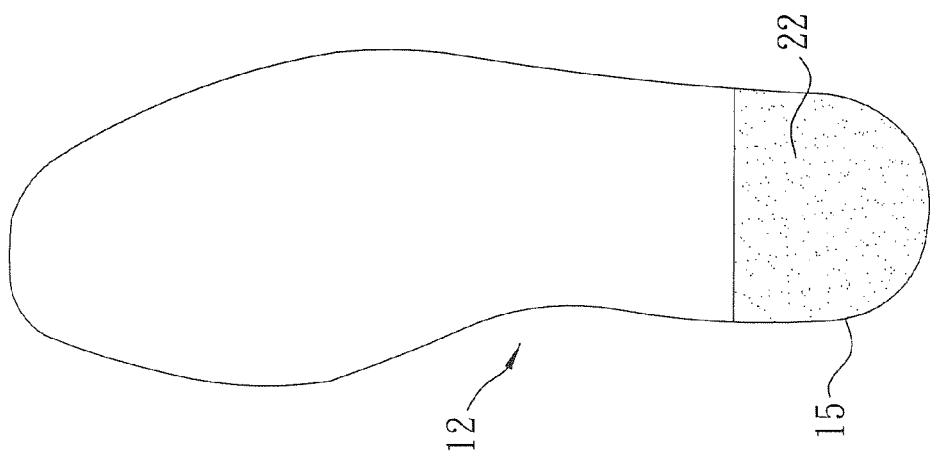
FIG. 6 is a schematic view, illustrating a heel pad attached to a heel area of the insole.

(vi) The shapes of the footprints 41 are inspected to determine whether there is any abnormal protrusion. An inclination angle of the big toe 413 relative to the second longitudinal reference line 35 is analyzed to determine an angle of deviation of the big toe 413. If the inclination angle of the big toe 413 is greater than 20°, the big toe 413 has hallux valgus. Referring to FIG. 6, it is observed that the left foot slants at an angle greater than 20°, so that the big toe 413 of the left foot has hallux valgus. Further, it is observed that there is a protrusion at a front inner side of the heel region 411 of the right footprint 41. This means that there is protrusion of the navicular bone.

Step III

A proper balancing pad(s) is selected from a set of the balancing pads 22, 23, 24, 25, 26, and is attached to the insole 12 at a location(s) where the user's foot has a foot imbalance. Selection of the balancing pad(s) can be done according to the following information:

1) If the body weight falls at the rear side of the footprint 41, one heel pad 22 may be attached to the insole 12 at a position corresponding to the heel area 15, as shown in FIG. 6. If the pressure exerted by the body weight is high, more heel pads 22 may be stacked and attached to the insole 12 to compensate for this high pressure.

Figure 7:
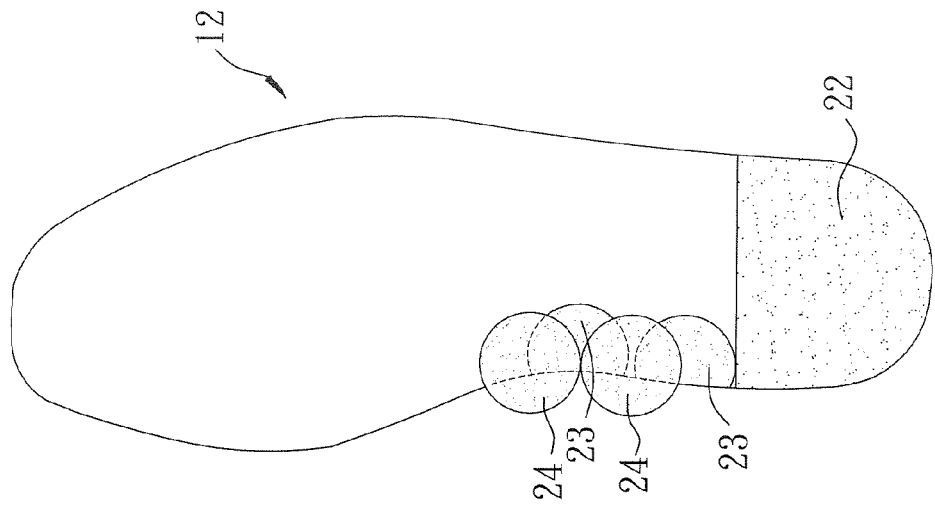
FIG. 7 is a schematic view similar to FIG. 6, but illustrating two lateral supporting pads and two micro-adjustment pads attached to an inner lateral side of the insole anteriorly of the heel pad.

2) If the body weight deviates toward the inner lateral side of the footprint 41, two lateral supporting pads 23 may be attached side-by-side to the left rear-half section 182 (see FIG. 3) of the insole 12 anteriorly of the heel pad 22. In addition, two micro-adjustment pads 24 may be disposed on top of the lateral supporting pads 23 in a stagger such that a one-third portion of each micro-adjustment pad 24 protrudes out of the insole 12, as shown in FIG. 7. When the insole 12 is inserted into the shoe assembly, the one-third portion of the micro-adjustment pads 24 will flex upward and abut against the outsole 11 and the sole liner 13 (see FIG. 13) of the shoe assembly. The number of the lateral supporting pads 23 and the micro-adjustment pads 24 may be increased or decreased depending on the size of the insole 12.

Figure 8:
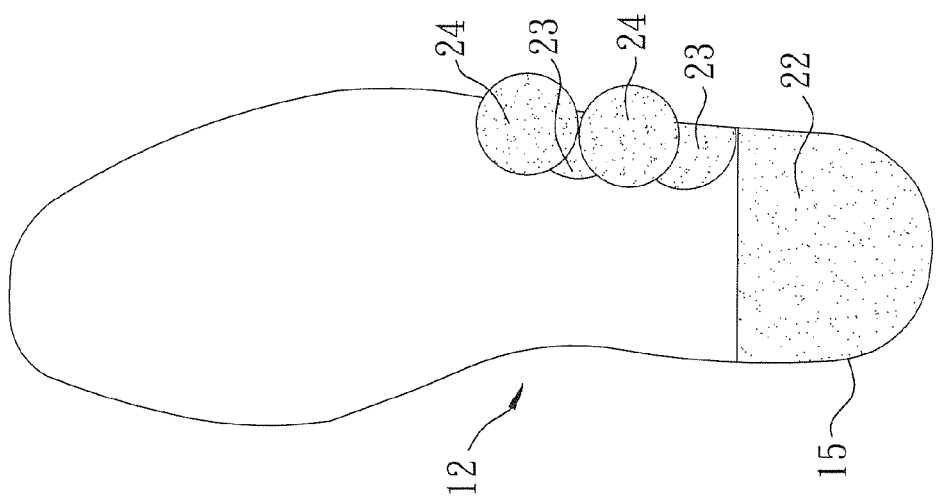
FIG. 8 is a view similar to FIG. 7, but illustrating the lateral supporting pads and the micro-adjustment pads attached to an outer lateral side of the insole anteriorly of the heel pad.

3) If the body weight deviates toward the outer lateral side of the footprint 41, two lateral supporting pads 23 may be attached side-by-side to the right rear-half section 181 (see FIG. 3) of the insole 12 anteriorly of the heel pad 22. In addition, two micro-adjustment pads 24 may be disposed on top of the lateral supporting pads 23 in a stagger such that a one-third portion of each micro-adjustment pad 24 protrudes out of the insole 12, as shown in FIG. 8. The number of the lateral supporting pads 23 and the micro-adjustment pads 24 may be increased or decreased depending on the size of the insole 12.

Figure 9:
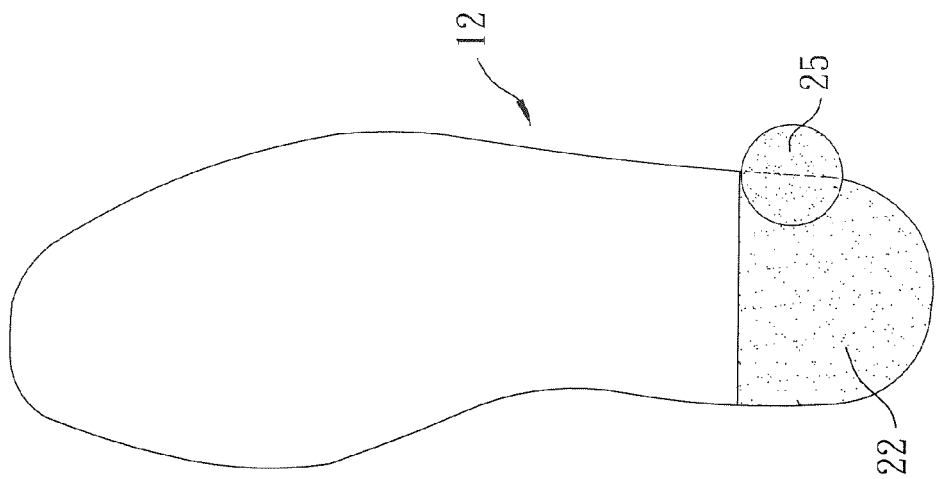
FIG. 9 is a view similar to FIG. 6, but illustrating a rear adjustment pad attached to the heel pad.

4) If the big toe 413 has hallux valgus, one rear adjustment pad 25 is adhered to a front outer side of the heel pad 22, as shown in FIG. 9, with a one-third portion thereof protruding out of the insole 12.

Figure 10:
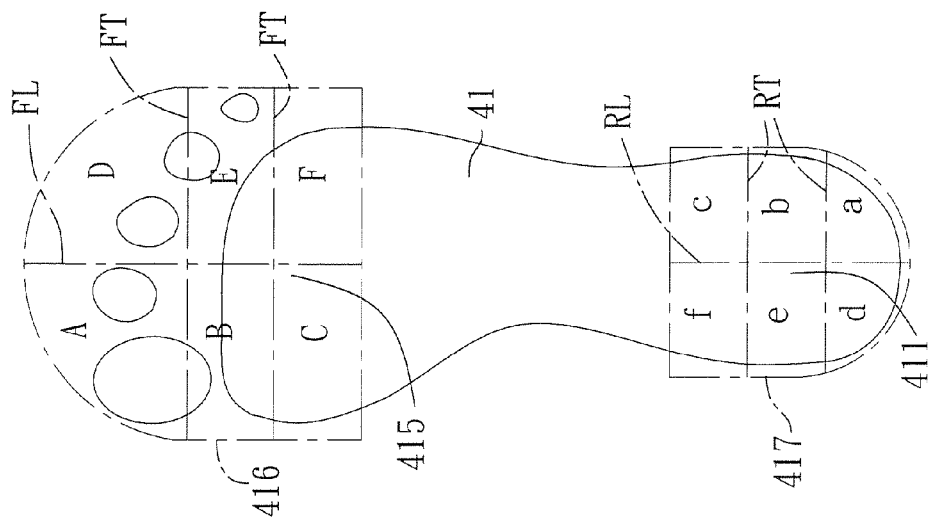
FIG. 10 is a schematic view, illustrating toe and heel regions of an initial footprint of the user's foot respectively put in a frame shown in a D-shaped imaginary line.

5) If the toe region 415 (see FIG. 10) of the footprint 41 indicates excessive foot pressure in this area of the user's foot 3, the below steps may be performed. As shown in FIG. 10, the toe region 415 is first put in a frame 416 shown by a D-shaped imaginary line, after which an imaginary front longitudinal line (FL) is drawn to divide the toe region 415 into inner and outer toe portions, and two parallel imaginary front transverse lines (FT) are drawn that intersect the imaginary front longitudinal line (FL), so that the toe region 415 is divided into front, medial, and rear inner toe portions (A, B, C), and front, medial, and rear outer toe portions (D, E, F). Thereafter, the heel region 411 is put in a frame 417 shown by another D-shaped imaginary line, after which an imaginary rear longitudinal line (RL) is drawn to divide the heel region 411 into inner and outer heel portions, and two parallel imaginary rear transverse lines (RT) are drawn that intersect the imaginary rear longitudinal line (RL), so that the heel region 411 is divided into front, medial, and rear inner heel portions (f, e, d), and front, medial, and rear outer heel portions (c, b, a).

When the foot pressure is concentrated on the front inner toe portion (A), a proper balancing pad is adhered to the insole 12 at a position corresponding to the rear outer heel portion (a). When the foot pressure is concentrated on the medial inner toe portion (B), the proper balancing pad is adhered to the insole 12 at a position corresponding to the medial outer heel portion (b). When the foot pressure is concentrated on the rear inner toe portion (C), the proper balancing pad is adhered to the insole 12 at a position corresponding to the front outer heel portion (c). When the foot pressure is concentrated on the front outer toe portion (D), the proper balancing pad is adhered to the insole 12 at a position corresponding to the rear inner heel portion (d). When the foot pressure is concentrated on the medial outer toe portion (E), the proper balancing pad is adhered to the insole 12 at a position corresponding to the medial inner heel portion (e). When the foot pressure is concentrated on the rear outer toe portion (F), the proper balancing pad is adhered to the insole 12 at a position corresponding to the front inner heel portion (f).

Figure 11:
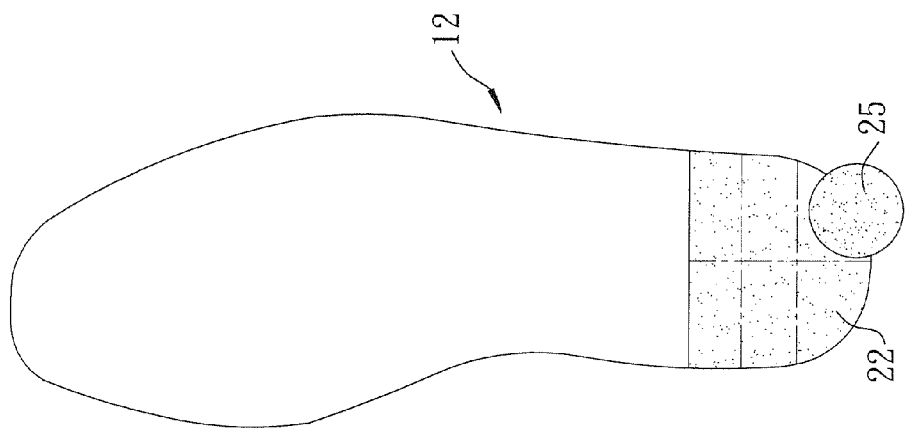
FIG. 11 is a schematic view, illustrating the rear adjustment pad attached to the insole at a position corresponding to a rear outer heel portion of the heel region.

With reference to FIGS. 10 and 11, when the foot pressure falls on the big toe 413 (see FIG. 5), that is, at the front inner toe portion (A), the rear adjustment pad 25 is adhered to the heel pad 22 at a position corresponding to the rear outer heel portion (a). If the medial inner toe portion (B) bears the foot pressure, the rear adjustment pad 25 is adhered to the insole 12 at a position corresponding to the medial outer heel portion (b) with the one-third portion thereof protruding out of the insole 12.

Figure 12:
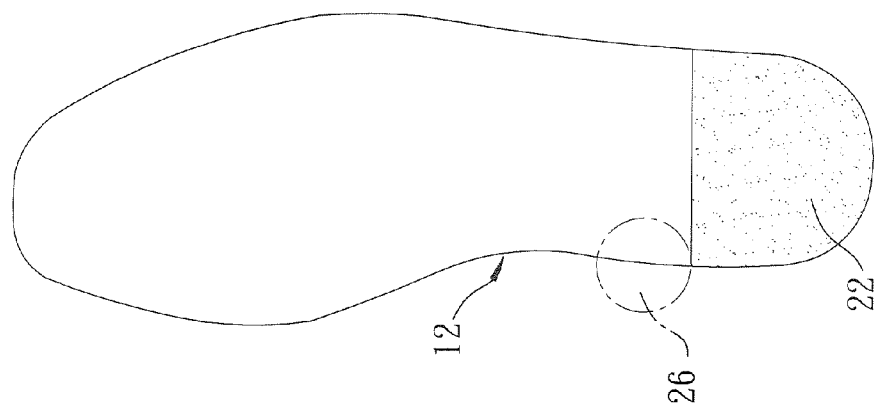
FIG. 12 is a view similar to FIG. 6, but illustrating a navicular bone supporting pad disposed at a position corresponding to a front inner heel portion of the heel region.

6) When the navicular bone has a protruding problem, with reference to FIGS. 1 and 12, a navicular bone supporting pad 26 may be adhered to the bottom portion of the foot arch correction device 14 at a position corresponding to the inner lateral side of the insole 12 anteriorly of the heel pad 22.

Step IV

After the initial footprint 41 of the user's foot 3 is analyzed to obtain the initial information and after the balancing pads (22, 23, 24, 25, 26) are selected properly and attached to the sole unit(s) 11, 12, 13 of the foot correcting and balancing shoe assembly at proper locations, the user is allowed to wear the foot correcting and balancing shoe assembly to carry out an initial correction and adjustment for the user's foot 3.

Figure 13:
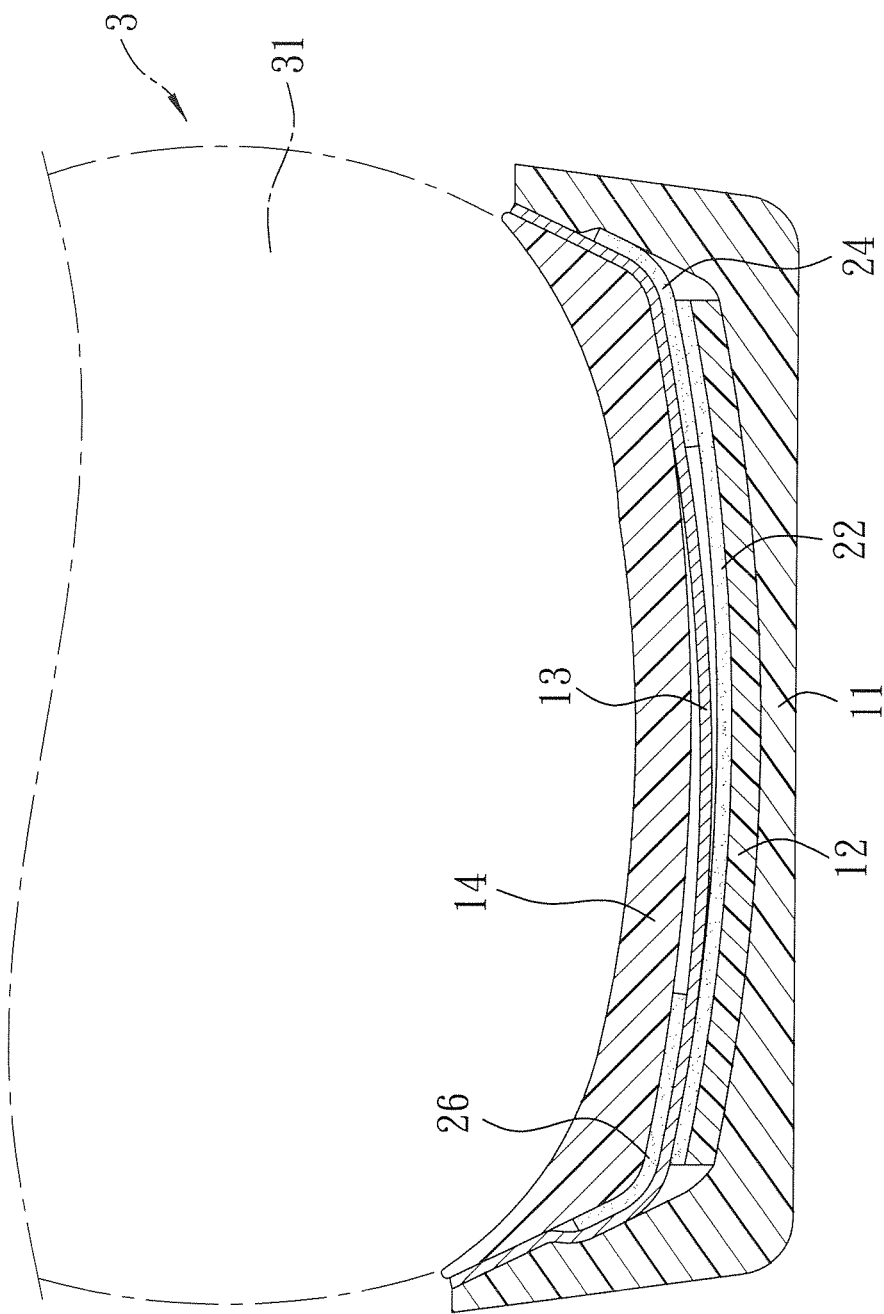
FIG. 13 is a sectional view of the foot correcting and balancing shoe assembly shown in FIG. 1.

With reference to FIG. 13, in combination with FIG. 1, when the user wears the foot correcting and balancing shoe assembly of the present invention, particular regions of the user's foot 3 are supported by the balancing pads 22, 23, 25, 26, while the one-third portions of the micro-adjustment pads 24 are used to push a portion of the outer lateral side of the user's foot 3 toward the center for correction and adjustment.

When the user walks while wearing the left and right shoe assemblies of the present invention, as the user's feet completely contact the ground, the foot arches become flattened, and the muscles and tendons of the foot arches are also stretched to absorb the user's body weight during walking. When one of the user's heels 31 is raised from the ground, these soft tissues will gather up, and energy is converted into force that pushes the user's body to move forward. Each time a step is taken, as shown by arrows in FIGS. 1 and 3, the pressure conversion of the foot 3 starts from the heel 31 toward the front along an outer lateral side of the foot 3, and then toward the inner lateral side along the toe region 415 until reaching a position below the big toe 413. Because the heel 31 of the foot 3 is nearest the user's body, the weight of the body is mainly supported by the heel 31. The direction of the force exerted by the heel 31 will determine the distribution direction of the foot pressure, so that the weight can be displaced through the heel pad 22. When the foot pressure moves forwardly, through the support of the lateral supporting pads 23 and the micro-adjustment pads 24, the weight of the user's body can be moved forwardly and inwardly. However, because the inner side of the foot arch correction device 14 is raised, and through a balance mechanism of human dynamics and ergonomics, the foot 3 is urged to correct by itself to deviate outwardly so that the force is outward. Further, through the navicular bone supporting pad 26 that supports the navicular bone, the foot arch can be corrected and restored to normal. Moreover, by adhering the rear adjustment pad 25 to the rear outer portion of the insole 12, similarly, through the human balance mechanism, the force at the big toe 413 is pulled back so as to reduce the pressure borne by the big toe 413.

Aside from using the foot arch correction device 14 to correct the foot shape, the balancing pads 22, 23, 24, 25, 26 are used to support portions of the user's foot, so that foot imbalance can be corrected. This results in the external rotation of the tibia and the pelvis, so that friction among the bones maybe prevented. Hence, the soft tissues around the knee joint can be adjusted, tension of the tendons, ligaments, and muscles can be lowered, and pain and swelling may be reduced.

After the foot correcting and balancing shoe assembly is used for a period of time, for example, three months, the foot imbalance problem may be alleviated or completely removed.

Step V

Figure 15:
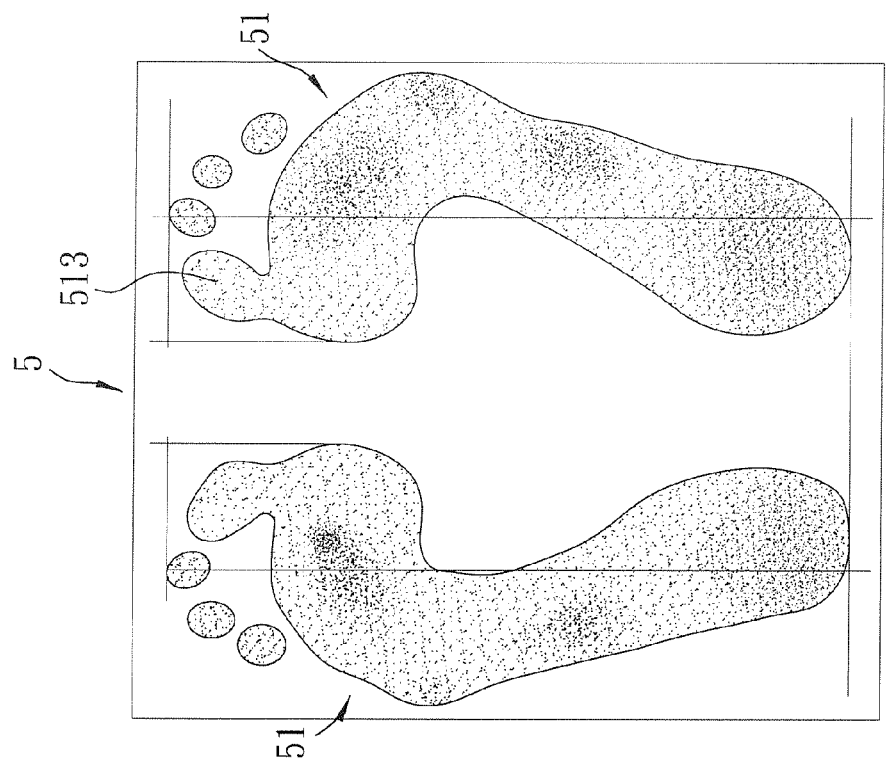
FIG. 15 is a view similar to FIG. 14, but illustrating a contour line drawn around a periphery of each initial footprint.
Figure 14:
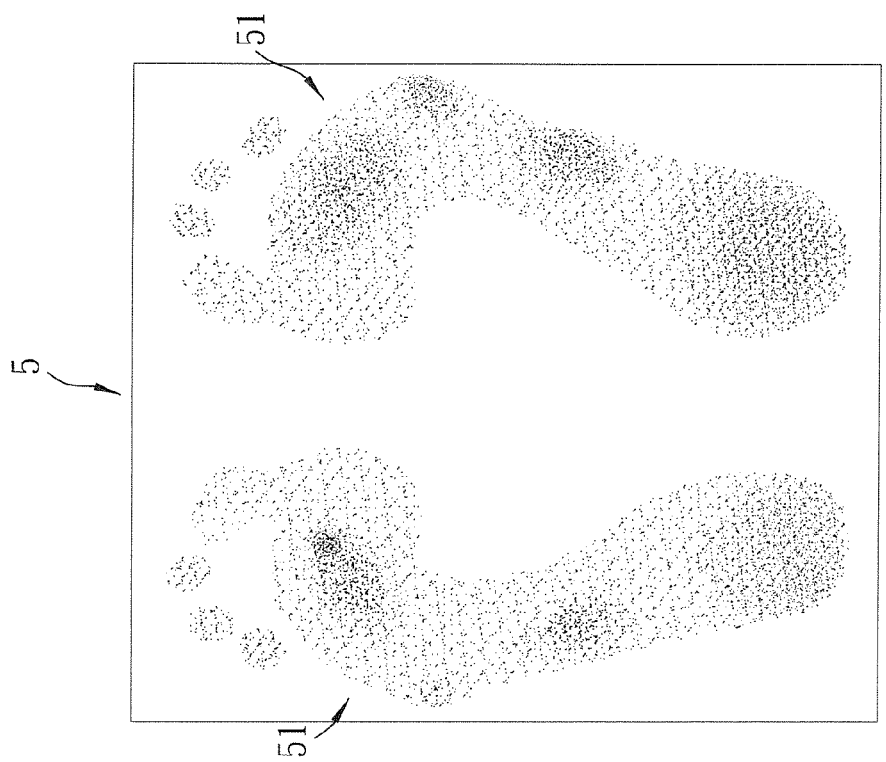
FIG. 14 is a schematic view of new footprints of the user's feet obtained in the first preferred embodiment of the method of the present invention.
Figure 16:
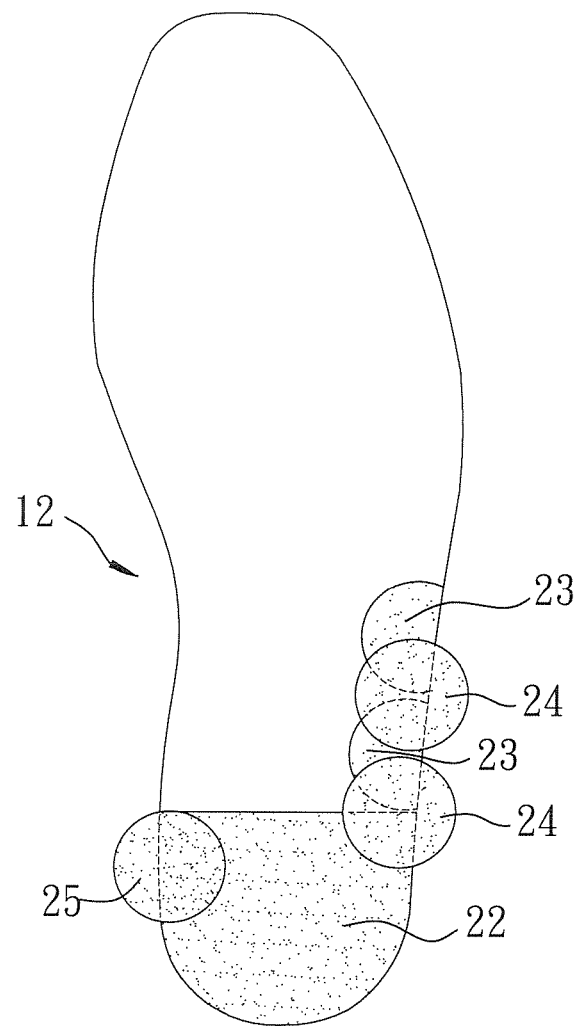
FIG. 16 shows re-selected balancing pads re-located on the insole.

If the foot imbalance problem is found to be alleviated, re-adjustment may be carried out as follows: New footprints 51 of the user's feet are printed on a sheet of paper 5, as shown in FIG. 14, after the user has used the foot correcting and balancing shoe assembly for a certain period, for example, 2-3 months. Contour lines of the new footprints 51 are drawn, as shown in FIG. 15.

Step VI

The shape and the darkness of the ink in each footprint 51 are analyzed to obtain re-adjustment information as to the progress of the user's foot 3 which has the foot imbalance. The re-adjustment information is compared with the initial information. From the comparison, the progress of the user's foot 3 can be observed. For example, it can be noted that, while the body weight is still at the rear of the heel 31, the foot pressure has been minimized, the foot arch of the user's foot 3 has been corrected to be close to a normal arch, the navicular bone has been raised, the big toe 513 of the right footprint 51 is not subjected to too much foot pressure, and the body weight that initially deviates inwardly is now deviating outwardly. According to the comparison, re-adjustment may be made by re-arranging the balancing pads. For re-arrangement, one or more balancing pad (s) may be re-selected from the set of the balancing pads 22, 23, 24, 25, 26 according to the re-adjustment information.

Step VII

In this step, the balancing pads 22, 23, 24, 25, 26 previously used in step III are removed from the sole unit of the shoe assembly, and according to the re-adjustment information, the re-selected balancing pad(s) are re-located on the sole unit. For example, referring to FIG. 16 in combination with FIG. 3, the re-selected balancing pads re-located on the insole 12 include the heel pad 22, the two lateral supporting pads 23, the two micro-adjustment pads 24, and the rear adjustment pad 25. Only the navicular bone supporting pad 26 shown in FIG. 3 is removed from the shoe assembly. The rear adjustment pad 25 on the heel pad 22 is moved to a position corresponding to the front inner heel portion (f) (see FIG. 10). The heel pad 22, the lateral supporting pads 23, and the micro-adjustment pads 24 are maintained at the original positions thereof. When the user wears the shoe assembly with the re-located balancing pads 22, 23, 24, 25, the height of the user's foot in particular regions can be adjusted, so that the pressure on the user's foot can be re-balanced, and The abnormal parts of the user's foot 3 can be placed in their respective correct positions. Hence, when the user stands or walks, an excellent balance and stability can be obtained, and the user can walk comfortably without easily feeling tired.

A second preferred embodiment of the method for correcting and balancing the user's foot 3 according to the present invention includes the steps as outlined below.

Figure 17:
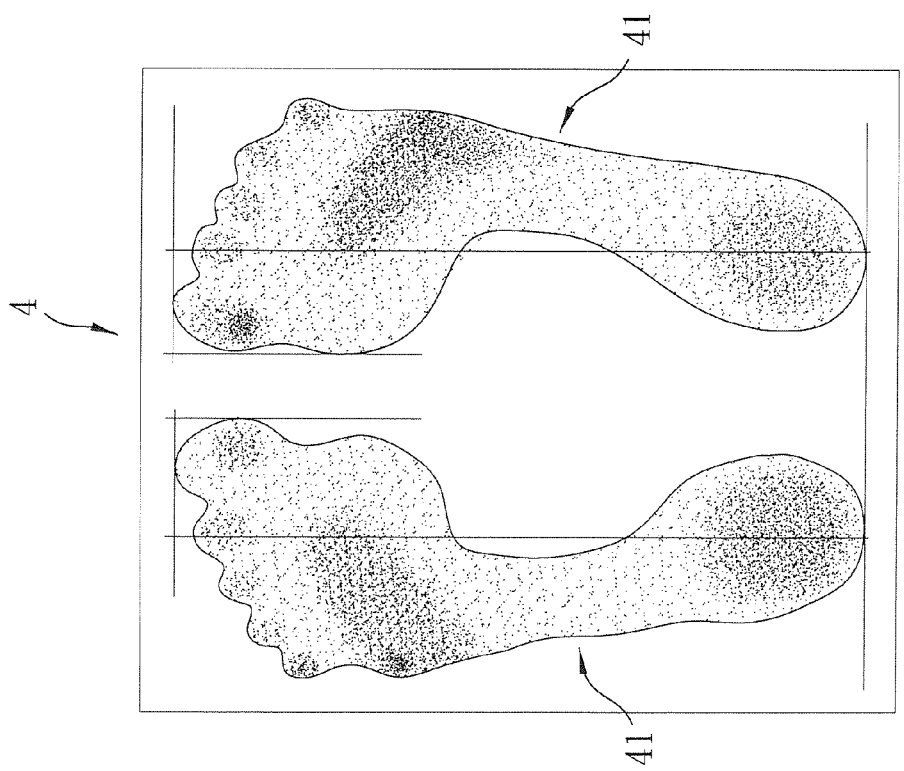
FIG. 17 is a schematic view of initial footprints of a user's feet obtained in the second preferred embodiment of a method of the present invention with contour lines respectively drawn around peripheries of the initial footprints.

Initial footprints 41 of the user's feet are obtained on a sheet of paper 4, as shown in FIG. 17.

Figure 18:
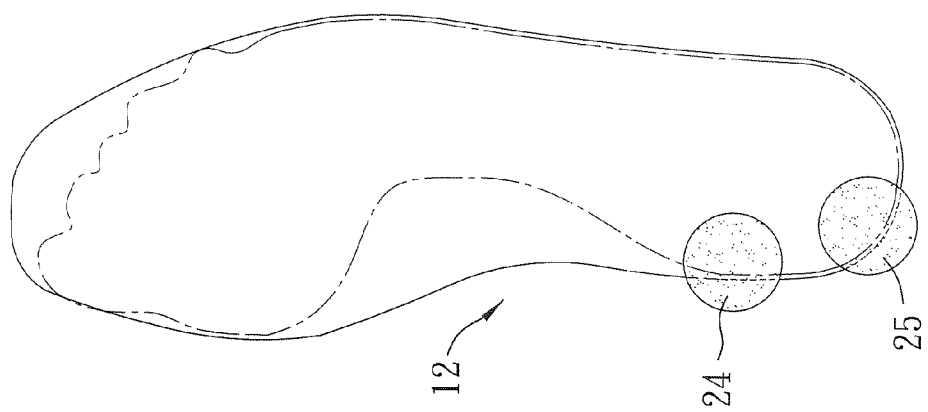
FIG. 18 illustrates a micro-adjustment pad and a rear adjustment pad attached to the insole at positions corresponding to a front inner heel portion and a rear inner heel portion of the heel region.

The shape and the darkness of the ink in each of the left and right initial footprints 41 are analyzed to obtain initial information. For example, referring to FIG. 17, the initial information indicates that the left and right footprints 41 have high arches, the foot pressure obviously deviates toward the outer side of each foot, and the little toe is subjected to stress. As shown in FIGS. 10 and 18, one micro-adjustment pad 24 is adhered to the front inner heel portion (f) of the insole 11 with a one-third port ion thereof protruding out of the insole 12, and one rear adjustment pad 25 is adhered to the rear inner heel portion (d) of the insole 12 with a one-third portion thereof protruding out of the insole 12.

When the user walks using the foot correcting and balancing shoe assembly of the present invention having the insole 12 adhered with the micro-adjustment pad 24 and the rear adjustment pad 25 to support the respective portions of the user's foot 3, through the balance mechanism of human dynamics and ergonomics, the user's feet can be automatically corrected so that the pressure deviates toward the inner side, thereby reducing the pressure upon the little toe.

Figure 19:
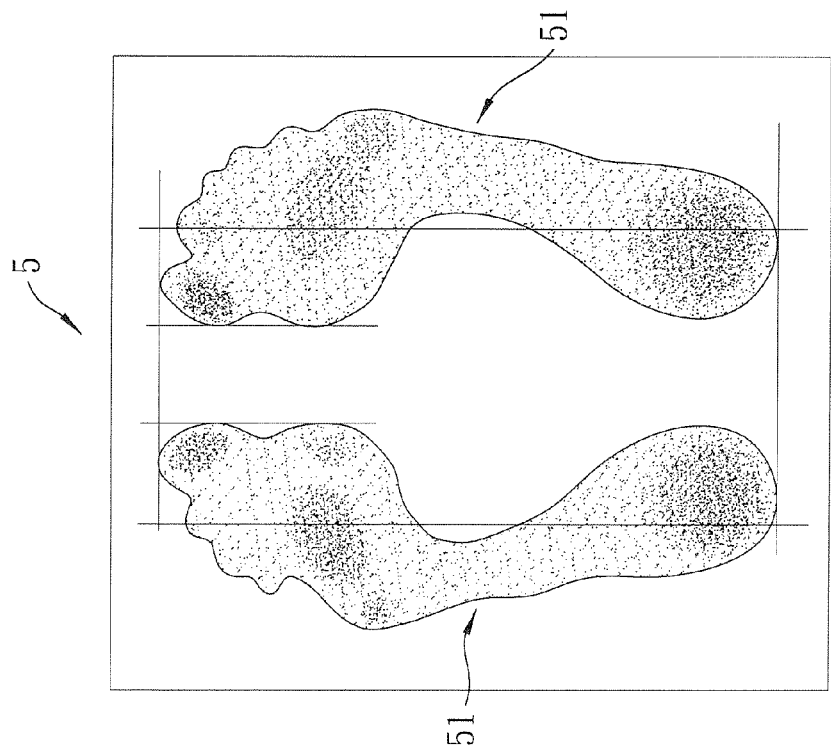
FIG. 19 is a schematic view of new footprints of the user's feet obtained in the second preferred embodiment of the method of the present invention.

After the user has used the corrected shoe assembly for a certain period, for example, three months, new footprints 51 of the user's feet are obtained on a sheet of paper 5, as shown in FIG. 19. The shape and the darkness of the ink in each of the left and right footprints 51 are analyzed to obtain re-adjustment information.

Figure 20:
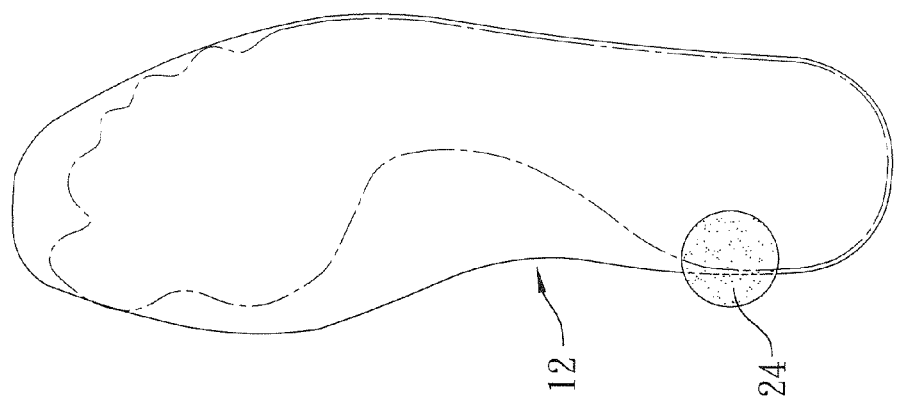
FIG. 20 is a view similar to FIG. 18, but illustrating the rear adjustment pad removed from the insole.

The re-adjustment information is compared with the initial information, and it is found that the pressure on the outer side of each foot is reduced, and the little toe bears no force. With reference to FIGS. 10 and 20, the micro-adjustment pad 24 is remained on the insole 12, and the rear adjustment pad 25 (see FIG. 18) is removed from the insole 12. Through the human balance mechanism that permits the pressure to continuously move inward, the pressures on the user's feet can obtain a perfect balance.

A third preferred embodiment of the method for correcting and balancing the user's foot according to the present invention includes the steps as outlined below.

Figure 21:
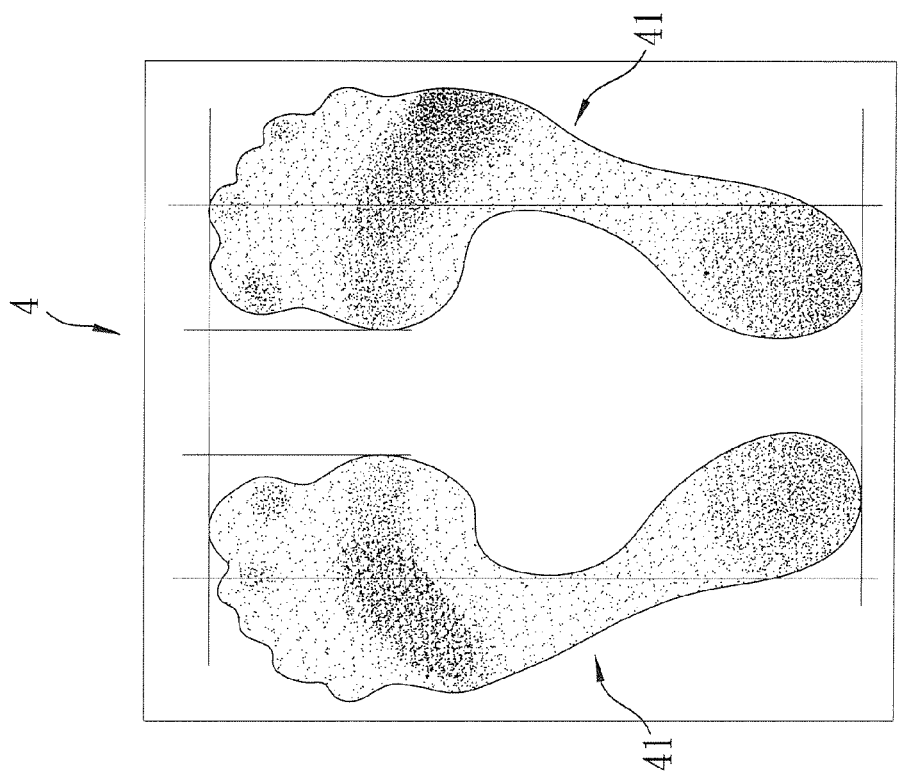
FIG. 21 is a schematic view of initial footprints of a user's feet obtained in the third preferred embodiment of a method of the present invention with contour lines respectively drawn around peripheries of the initial footprints.
Figure 24:
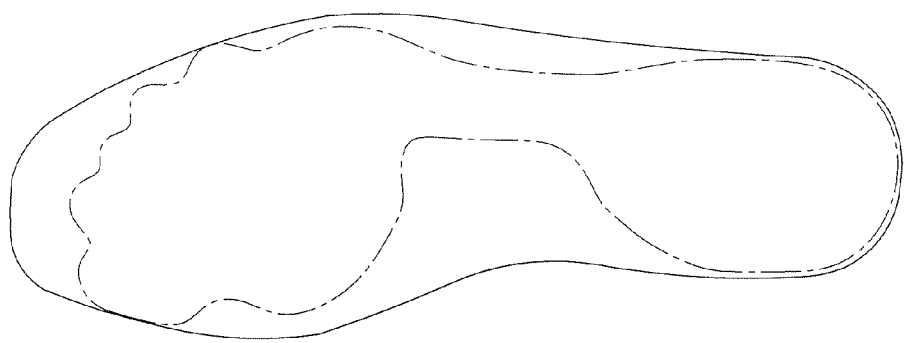
FIG. 24 is a view similar to FIG. 22, but illustrating the micro-adjustment pad removed from the insole.

Initial footprints 41 of the user's feet are obtained on a sheet of paper 4, as shown in FIG. 21.

Figure 22:
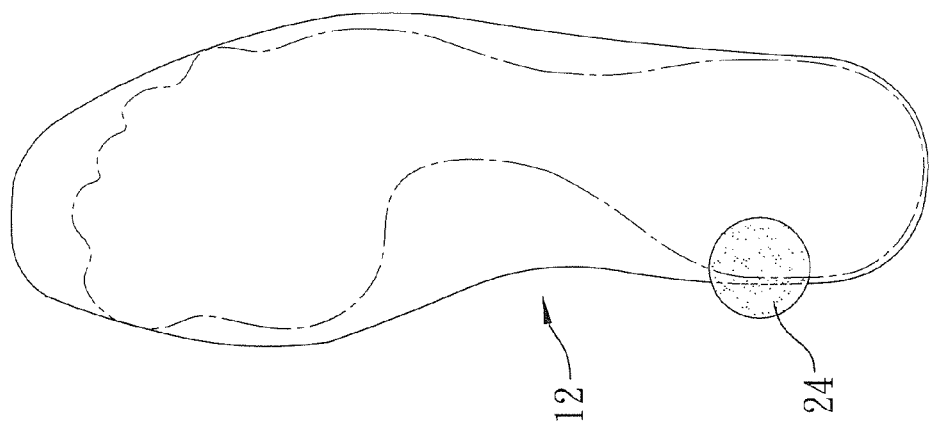
FIG. 22 is a schematic view, illustrating a micro-adjustment pad attached to the insole at a position corresponding to a front inner heel portion of the heel region.

The shape and the darkness of the ink in each of the left and right initial footprints 41 are analyzed to obtain initial information. The initial information indicates that the footprints 41 have high arches, and the force is toward the outer side. As shown in FIGS. 10 and 22, only one micro-adjustment pad 24 is adhered to the front inner heel portion (f) of the insole 12 with a one-third portion thereof protruding out of the insole 12.

When the user uses the corrected shoe assembly, through human balance mechanism of dynamics and ergonomics, the user's foot can be automatically corrected so that the force moves inwardly.

Figure 23:
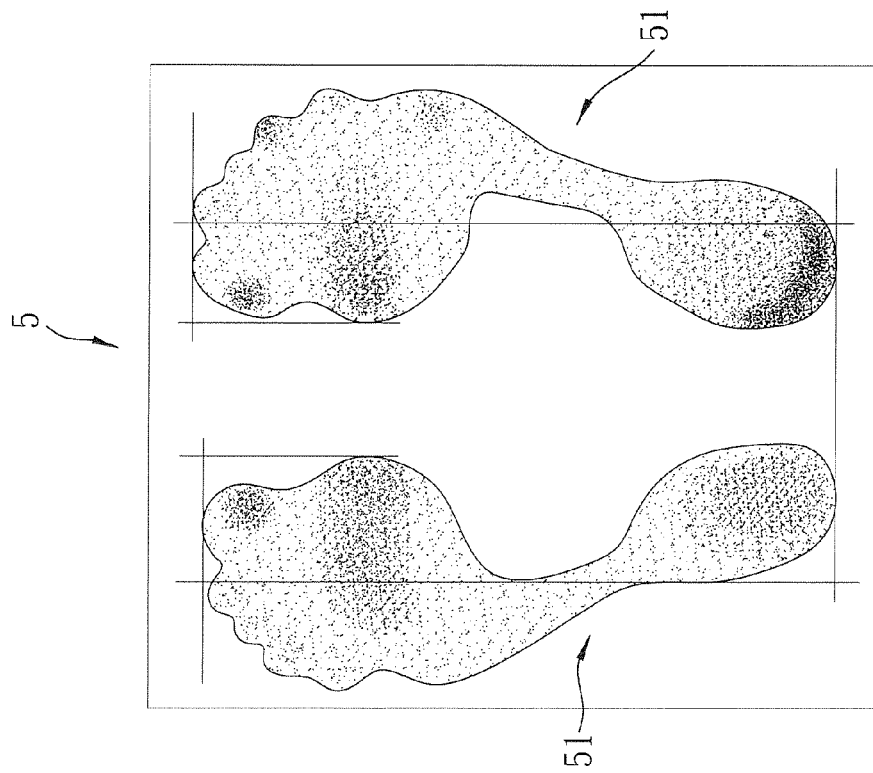
FIG. 23 is a schematic view of new footprints of the user's feet obtained in the third preferred embodiment of the method of the present invention.

After the user uses the corrected shoe assembly for a certain period, for example, one month, new footprints 51 of the user's feet are obtained on a sheet of paper 5, as shown in FIG. 23.

The shape and the darkness of the ink in each of the new footprints 51 are analyzed to obtain re-adjustment information. The re-adjustment information is compared with the initial information. The comparison indicates that the pressure has been reduced, and the stress has been shifted inward, so that the micro-adjustment pad 24 shown in FIG. 22 is not necessary and is therefore removed from the insole 12.

In sum, aside from using the foot arch correction device 14 to correct the shape of the footprint made by each user's foot 3, the present invention also uses the set of the balancing pads 22, 23, 24, 25, 26 to support the location (s) where the user's foot has foot imbalance. As such, the pressure at the user's foot can be restored from an imbalanced condition to a balanced condition, thereby bringing therealong the knee, the pelvis, and the spine to restore to their respective normal positions.

While the present invention has been described in connection with what are considered the most practical and preferred embodiments, it is understood that this invention is not limited to the disclosed embodiments but is intended to cover various arrangements included within the spirit and scope of the broadest interpretations and equivalent arrangements.

We claim:

1. A method of correcting and balancing a user's foot, comprising:
    obtaining an initial footprint of the user's foot, by placing the user's foot on a resilient fabric sheet containing ink so as to make an imprint the initial footprint of the user's foot on a sheet of paper;
    analyzing shape and darkness of the ink on the paper of the initial footprint to obtain initial information as to a location where the user's foot has foot imbalance; and
    selecting one or more appropriate balancing pad(s) from a set of balancing pads and applying the same to a sole unit of a foot correcting and balancing shoe assembly at the location where the user's foot has the foot imbalance;
    wherein the analyzing of the shape and darkness of the ink on the paper with the initial footprint of the user's foot includes:
        drawing a contour line around a periphery of the initial footprint;
        drawing a transverse reference line that passes through a rear end of the initial footprint, a first longitudinal reference line that passes centrally through the index toe of the initial footprint, and a second longitudinal reference line that passes through an inner lateral side of the initial footprint that is proximate to the big toe of the initial footprint and that is parallel to the first longitudinal reference line, the first and second longitudinal reference lines being perpendicular to the transverse reference line;
        analyzing areas of the left and right sides of the first longitudinal reference line to determine a tilting direction of the initial footprint,
        analyzing the darkness of the ink to determine the distribution of pressure on the foot of the initial footprint; and analyzing an inclination angle of the big toe relative to the second longitudinal reference line to determine an angle of deviation of the big toe.

2. The method of claim 1, further comprising performing re-adjustment including:
   obtaining a new footprint of the user's foot after the user has used the foot correcting and balancing shoe assembly for a certain period, and
   analyzing the shape and the darkness of ink on paper printed with the new footprint of the user's foot to obtain re-adjustment information as to the progress of the user's foot which has the foot imbalance, the re-adjustment information being compared with the initial information.

3. The method of claim 2, wherein the re-adjustment further includes re-arranging the balancing pad(s) on the sole unit.

4. The method of claim 3, wherein the re-arranging of the balancing pad(s) includes:
   re-selecting at least one balancing pad from a set of the balancing pads according to the re-adjustment information, and re-locating the re-selected balancing pad on the sole unit.

5. The method of claim 2, wherein the re-adjustment further includes removing the balancing pad from the sole unit when the comparison between the re-adjustment information and the initial information indicates that the foot imbalance problem of the user's foot has been corrected.

6. The method of claim 1, wherein the sole unit includes a heel area, the appropriate balancing pad including a heel pad for attachment to the heel area.

7. The method of claim 1, wherein the sole unit includes a heel area, the appropriate balancing pad including at least one lateral supporting pad for attachment to a lateral side of the sole unit anteriorly of the heel area.

8. The method of claim 7, wherein the appropriate balancing pad further includes at least one micro-adjustment pad to be stacked on the lateral supporting pad.

9. The method of claim 1, wherein the sole unit includes a heel area, the appropriate balancing pad including at least one rear adjustment pad for attachment to a lateral side of the sole unit within the heel area.

10. The method of claim 1 wherein the sole unit includes a heel area, the appropriate balancing pad including at least one navicular bone supporting pad for attachment to a lateral side of the sole unit anteriorly of the heel area.

11. The method of claim 1, wherein the foot correcting and balancing shoe assembly includes a plurality of the sole units, the sole units including an outsole, an insole, and a sole liner, the foot correcting and balancing shoe assembly further including a foot arch correction device mounted to the sole liner, the appropriate balancing pad being attached to the insole.

12. A method of correcting and balancing a user's foot, comprising:
   obtaining an initial footprint of the user's foot by placing the user's foot on a resilient fabric sheet containing ink so as to make an imprint of the initial footprint of the user's foot on a sheet of paper;
   drawing an imaginary front longitudinal line to divide a toe region of the initial footprint into inner and outer toe portions;
   drawing two parallel imaginary front transverse lines that intersect the imaginary front longitudinal line so that the toe region is divided into front, medial, and rear inner toe portions, and front, medial, and rear outer toe portions,
   drawing an imaginary rear longitudinal line to divide a heel region of the initial footprint into inner and outer heel portions;
   drawing two parallel imaginary rear transverse lines that intersect the imaginary rear longitudinal line so that the heel region is divided into front, medial, and rear inner heel portions, and front, medial, and rear outer heel portions;
   analyzing the shape and the darkness of the ink on the paper with the initial footprint of the user's foot to obtain initial information as to a location where the user's foot has foot imbalance; and
   applying an appropriate balancing pad to a sole unit of a foot correcting and balancing shoe assembly based on the initial information regarding location of foot imbalance,
   wherein, the appropriate balancing pad is applied to a rear outer heel portion when a foot pressure is concentrated on the front inner toe portion, to a middle outer heel portion when the foot pressure is concentrated on the middle inner toe portion, to a front outer heel portion when the foot pressure is concentrated on the rear inner toe portion, to a rear inner heel portion when the foot pressure is concentrated on the front outer toe portion, to a middle inner heel portion when the foot pressure is concentrated on the middle outer toe portion, and to a front inner heel portion when the foot pressure is concentrated on the rear outer toe portion.

13. The method of claim 12, further comprising performing re-adjustment including:
   obtaining a new footprint of the user's foot after the user has used the foot correcting and balancing shoe assembly for a certain period, and
   analyzing the shape and the darkness of ink on paper printed with the new footprint of the user's foot to obtain re-adjustment information as to the progress of the user's foot which has the foot imbalance, the re-adjustment information being compared with the initial information.

14. The method of claim 13, wherein the re-adjustment further includes re-arranging the balancing pad(s) on a sole unit of the foot correcting and balancing shoe assembly.

15. The method of claim 14, wherein the re-arranging of the balancing pad(s) includes:
   re-selecting at least one balancing pad from a set of the balancing pads according to the re-adjustment information, and
   re-locating the re-selected balancing pad on the sole unit.

16. The method of claim 13, wherein the re-adjustment further includes removing the balancing pad from the sole unit when the comparison between the re-adjustment information and the initial information indicates that the foot imbalance problem of the user's foot has been corrected.

* * * * *